(12) United States Patent
Ueno et al.

(10) Patent No.: US 6,469,062 B2
(45) Date of Patent: Oct. 22, 2002

(54) USE OF 15-KETO-PROSTAGLANDINS IN PROMOTING BILE SECRETION

(75) Inventors: Ryuji Ueno, Montgomery, MD (US); Makoto Suematsu, Tokyo-to (JP)

(73) Assignee: Sucampo A.G., Zug (CH)

( * ) Notice: Subject to any disclaimer, the term of this patent is extended or adjusted under 35 U.S.C. 154(b) by 0 days.

(21) Appl. No.: 09/827,375

(22) Filed: Apr. 6, 2001

(65) Prior Publication Data

US 2002/0004524 A1 Jan. 10, 2002

Related U.S. Application Data

(60) Provisional application No. 60/194,894, filed on Apr. 6, 2000.

(51) Int. Cl.$^7$ ............................................. A61K 31/215
(52) U.S. Cl. ....................................................... 514/530
(58) Field of Search ......................................... 514/530

(56) References Cited

U.S. PATENT DOCUMENTS

| | | | |
|---|---|---|---|
| 4,503,068 A | 3/1985 | Sakai et al. | |
| 5,073,569 A | 12/1991 | Ueno et al. | 514/530 |
| 5,096,927 A * | 3/1992 | Ueno et al. | 514/530 |
| 5,166,174 A | 11/1992 | Ueno et al. | 514/530 |
| 5,212,324 A | 5/1993 | Ueno | 554/118 |
| 5,221,763 A | 6/1993 | Ueno et al. | 560/121 |
| 5,739,161 A | 4/1998 | Ueno | 514/530 |

FOREIGN PATENT DOCUMENTS

| | | | |
|---|---|---|---|
| EP | 0 424 156 A | 4/1991 | |
| EP | 0 690 049 | 1/1996 | |
| JP | 63-27433 | 2/1988 | A61K/31/557 |
| JP | 6-9404 | 1/1994 | A61K/31/557 |

OTHER PUBLICATIONS

Lou Jinning et al. "Inhibition of leukocyte adherence and transendothelial migration in cultured human liver vascular endothelial cells by prostaglandin E1." Hepatology, vol. 27, No. 3, Mar. 1998 pp. 822–828, XP001057106 ISSN: 0270–9139 p. 822, col. 2, paragraph 1; p. 827, col. 2 last paragraph.

PCT International Search Report.

Kaminski, Donald et al., The Effect of Prostaglandin $A_1$ and $E_1$ on Canine Hepatic Bile Fow, Journal of Surgical Research 18, 391–397 (1975).

Kaminski, D.L. et al., "The Effect of Prostaglandin $F_{2\alpha}$ on Canine Hepatic Bile Flow and Biliary Cyclic AMP Secretion", Journal of Surgical Research 22, 545–553 (1977).

Kaminski, D.L. et al., "The Relationship Between Glucagon and Prostaglandin F in Stimulating Canine Hepatic Bite Flow", Hepatology, vol. 6, No. 2, pp. 275–281, 1986.

Kaminski, Donald, et al., "The Effects of Prostacyclin on Canine Hepatic Bile Flow", Hepatology, vol. 4, No. 4, pp. 644–650, 1984.

Tamaki, T., et al., "Hypothermic Preservation of the Rat Liver Assessed by Orthotopic Transplanation", Transplantation, vol. 46, No. 4, 626–628, 1988.

Kawachi, S., et al., "Efficacy of Infusion of Prostaglandin $E_1$ to Improve the Hepatic Blood Flow and Graft Viability in Porcine Liver Transplantation", Transplantation, vol. 64, 205–209, No. 2, Jul. 27, 1997.

Krarup, N. et al., "Secretin–like Choleretic Effect of Prostaglandins $E_1$ and $E_2$ in Cats", J. Physiol., (1976) 254, pp. 813–820.

Kumamoto, Yusuke, et al., "Kupffer Cell–Independent Acute Hepatocellular Oxidative Stress and Decreased Bile Formation in Post–Cold–Ischemic Rat Liver", Hepatology, vol. 30, No. 6, 1999 1454–1463.

Beckh, Karlheinz, et al. "Direct Regulation of Bile Secretion by Prostaglandins in Perfused Rat Liver", Hepatology vol. 19, No. 5, 1994.

* cited by examiner

*Primary Examiner*—Marianne C. Seidel
*Assistant Examiner*—Brian-Yong S. Kwon
(74) *Attorney, Agent, or Firm*—Sughrue Mion, PLLC

(57) ABSTRACT

Disclosed is a method for promoting bile secretion, which comprises administering an effective amount of a certain 15-keto-prostaglandin compound to a subject having a disease or condition associated with bile secretion deficient. Also disclosed is a method for treatment of a liver to be transplanted in a liver transplantation process, which comprises contacting the liver with a liquid composition comprising the 15-keto-prostaglandin compound as above.

21 Claims, 4 Drawing Sheets

*p<0.05 Student's t-test (vs. control group)

()=number of animals tested

**p<0.01, *<0.05 vs. vehicle group by one way ANOVA with Fisher's multiple comparison test.

*p<0.05 vs. control group by one way ANOVA with Fisher's multiple comparison test.

†<0.1, *p<0.05 vs. control group by one way ANOVA with Fisher's multiple comparison test †<0.1, *p<0.05 vs. control group by one way ANOVA with Fisher's multiple comparison test

USE OF 15-KETO-PROSTAGLANDINS IN PROMOTING BILE SECRETION

CROSS REFERENCE TO RELATED APPLICATIONS

This application is an application filed under 35 U.S.C. 111(a) claiming benefit pursuant to 35 U.S.C. 119(e)(1) of the filing date of the Provisional Application 60/194,894, filed Apr. 6, 2000, pursuant to 35 U.S.C. 111(b).

FIELD OF THE INVENTION

The present invention relates to a new use of a 15-keto-prostaglandin compound as a bile secretion promoter.

BACKGROUND OF THE INVENTION

Bile is produced by hepatocyte and discharged in the bile duct, and is a colloidal solution containing various and complex ingredients. Producing bile is one of the most important functions in the various liver functions. The bile secreted from the liver is consisting of 97% of water and other ingredients including bile salt, bile pigment, phosphatidylcholine, cholesterol, trace albumins, electrolytes and the like. The main function of the bile is promoting fatty acid digestion and absorption by bile acid. Bile acid has a cholagogic property which induce bile acid-dependent bile secretion. Bile can also be secreted independently of bile acid and said secretion is referred to as bile acid-independent bile secretion. It has been known that reduce of bile secretion which could be caused by blockage of cystic duct, failure of cholecyst constriction, hepatocellular dependent icterus or the like, may cause various failures and diseases such as fatty acid malabsorption.

On the other hand, it has been known that hepatectomy and liver transplantation may cause ischemia-reperfusion cellular injury. Free radical may contribute to etiology of the cellular injury; when free radical is overproduced in the body, it attacks biomolecules and tissues, especially lipids in the biomembrane, to induce cell membrane injury and at the same time it produces lipid peroxide, which causes various failures and diseases in the body. In addition, hepatic failure induced by free radical, which is evoked by ischemia-reperfusion injury, may cause significant reduce of bile secretion. Therefore, to retain liver function, especially bile secreting ability during the liver transplantation process and after implantation of the liver is becoming very important object to be achieved.

Prostaglandins (hereinafter, referred to as PG(s)) are members of class of organic carboxylic acids, which are contained in tissues or organs of human or most other animals, and exhibit a wide range of physiological activity. PGs found in nature (primary PGs) generally have a prostanoic acid skeleton as shown in the formula (A):

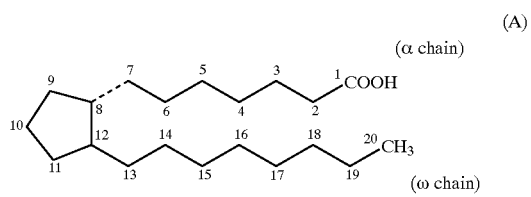

(A)

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

subscript 1: 13,14-unsaturated-15-OH
subscript 2: 5,6- and 13,14-diunsaturated-15-OH
subscript 3: 5,6-, 13,14- and 17,18-triunsaturated-15-OH.

Further, the PGFs are classified, according to the configuration of the hydroxy group at position 9, into α type (the hydroxy group is of a α-configuration) and β type (the hydroxy group is of a β-configuration).

$PGE_1$, $PGE_2$ and $PGE_3$ are known to have vasodilation, hypotension, gastric secretion decreasing, intestinal tract movement enhancement, uterine contraction, diuretic, bronchodilation and anti ulcer activities. $PGF_{1\alpha}$, $PGF_{2\alpha}$ and $PGF_{3\alpha}$ have been known to have hypertension, vasoconstriction, intestinal tract movement enhancement, uterine contraction, lutein body atrophy and bronchoconstriction activities.

In addition, some 15-keto prostaglandins (i.e. those having an oxo group at position 15 in place of the hydroxy group) and 13,14-dihydro-15-keto-prostaglandins are known as substances naturally produced by enzymatic actions during in vivo metabolism of primary PGs. 15-keto PGs have been disclosed in the specification of U.S. Pat. Nos. 5,073,569, 5,166,174, 5,221,763, 5,212,324 and 5,739,161. (These cited references are herein incorporated by reference.)

It has been known that a prostaglandin compound having hydroxy group at position 15 has a bile secretion promoting activity. For example, $PGE_1$, $PGE_2$, $PGA_1$, $PGF_{2\alpha}$, and prostacyclin have been reported to have an cholagogic effect in dogs and cats (J. Physiol. 254, 813–820,1976; J. Surg. Res. 18,391–397,1975; J. Surg. Res. 22,545–553, 1977; Hepatology 2, 275–281, 1986; Hepatology 4, 644–650, 1984; these cited references are herein incorporated by reference.)

In addition, intraportal administration of prostaglandin $E_1$ increased the bile flow in porcine of which liver was replaced by transplantation (Transplantation 64, 205–209, 1997, the cited reference is herein incorporated by reference). Further, in a rat liver transplantation model, addition of TEI-9063, a stabilized $PGI_2$ analogue, to a liver preservation solution improved bile producing activity of the implanted liver (Transplantation 46, 626–628, 1998, The cited reference is herein incorporated by reference.)

SUMMARY OF THE INVENTION

The inventor has studied on bioactivities of 15-keto prostaglandin compounds and found that 15-keto-prostaglandin compounds express a significant bile secretion promoting activity, and achieved to the invention. That is, the present invention provides a bile secretion promoting composition comprising a 15-keto-prostaglandin compound as an active ingredient. Said composition can be employed for treatment of liver to be transplanted.

The present invention also provides a method for promoting bile secretion comprising a step of administering an effective amount of a 15-keto prostaglandin compound to a subject having a disease or condition associated with bile secretion deficient.

The present invention also provides a method for treating a liver to be transplanted in a liver transplantation process comprising a step of contacting the liver with a liquid composition comprising a 15-keto-prostaglandin compound.

The present invention further provides use of a 15-keto-prostaglandin compound for producing a pharmaceutical composition for treatment of a subject having a condition or disease associated with bile secretion deficient.

Further more, the present invention provides use of a 15-keto-prostaglandin compound for producing a pharmaceutical composition for treating a liver to be transplanted in a liver transplantation process.

In the present invention, the "15-keto-prostaglandin compounds" (hereinafter, referred to as "15-keto-PG compounds") may include any of derivatives or analogs (including substituted derivatives) of a compound having an oxo group at 15-position of the prostanoic acid skeleton instead of the hydroxy group, irrespective of the configuration of the five membered ring, the number of double bonds, presence or absence of a substituent, or any other modification in the α ω or w chain.

The nomenclature of the 15-keto-PG compounds used herein is based on the numbering system of prostanoic acid skeleton represented in the above formula (A).

The formula (A) shows a basic skeleton of the C-20 carbon atoms, but the 15-keto-PG compounds in the present invention are never limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification these terms also include those PG related compounds having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11 -dehydroxy compound.

As stated above, the nomenclature of 15-keto-PG compounds is based on the prostanoic acid skeleton. However, in case the compound has a similar partial construction as a prostaglandin, the abbreviation of "PG" may be used. Thus, a PG compound of which a chain is extended by two carbon atoms, that is, having 9 carbon atoms in the α chain is nominated as 2-decarboxy-2-(2-carboxyethyl)-15-keto PG compound. Similarly, a compound having 11 carbon atoms in the αchain is nominated as 2-decarboxy-2-(4-carboxybutyl)-15-keto-PG compound. Further, a 15-keto-PG compound of which ω-chain is extended by two carbon atoms, that is, having 10 carbon atoms in the ω-chain is nominated as 15-keto-20-ethyl-PG compound. These compounds, however, may also be named according to the IUPAC naming system.

DETAILED DESCRIPTION OF THE INVENTION

Figure 1:
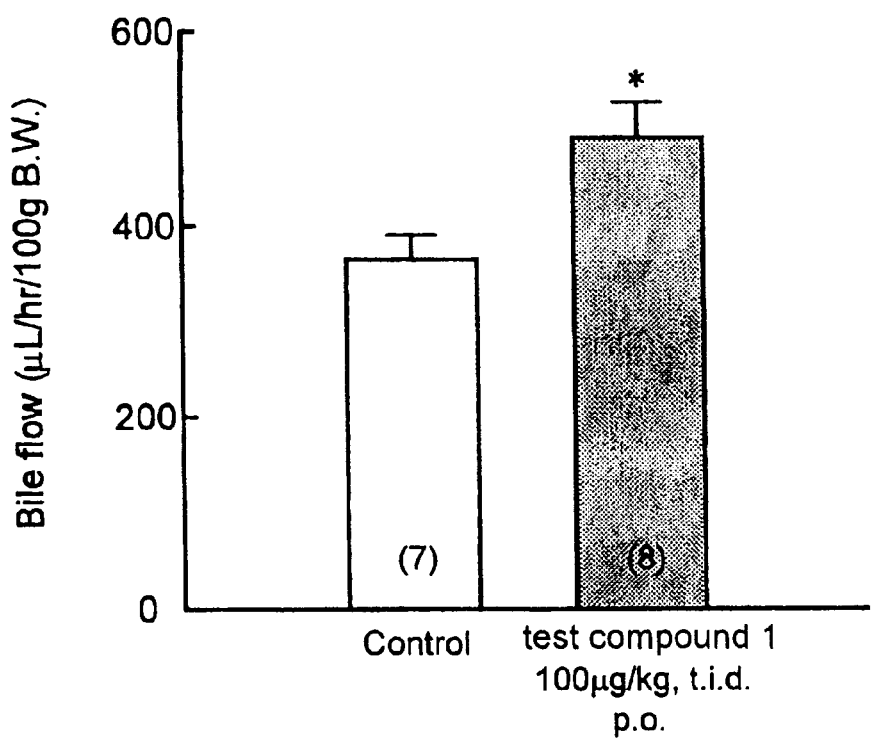
FIG. 1 represents the result of the Test Example 1, effect of the test compound 1(13,14-dihydro-15-keto-16,16-difluoro-18(S)-methyl-prostaglandin $E_1$) on bile flow in normal rats.

The 15-keto-PG compound used in the present invention may include any PG derivative or analog insofar as of which C-15 constitute carbonyl group, and may further include compounds having a 13,14-double bond(15-keto-PG type 1 compound), 13–14 and 5–6 double bonds(15-keto-PG type 2 compound), or 13–14, 5–6 and 17–18 double bonds (15-keto-PG type 3 compound) as well as a 13,14-single bond (13,14-dihydro-15-keto-PG compounds).

Typical examples of the compounds used in the present invention include 15-keto-PG type 1, 15-keto-PG type 2, 15-keto-PG type 3, 13,14-dihydro-15-keto-PG type 1, 13,14-dihydro-15-keto-PG type 2, 13,14-dihydro-15-keto-PG type 3 and the derivatives thereof.

Examples of the substitution compounds or derivatives include a 15-keto-PG compound of which carboxy group at the end of a chain is esterified; a compound of which a chain is extended; physiologically acceptable salt thereof; an unsaturated derivative having a double bond at 2–3 position or a triple bond at position 5–6, a PG compound having substituent(s) at position(s) 3, 5, 6, 16, 17, 18, 19 and/or 20; and a PG compound having lower alkyl or a hydroxy (lower) alkyl group at position 9 and/or 11 in place of the hydroxyl group.

According to the present invention, preferred substituents at positions 3, 17, 18 and/or 19 include alkyl having 1–4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include halogen atoms such as chlorine and fluorine. Preferred substituents at position 20 include saturated or unsaturated lower alkyl such as $C_{1-4}$ alkyl, lower alkoxy such as $C_{1-4}$ alkoxy, and lower alkoxy alkyl such as $C_{1-4}$ alkoxy-$C_{1-4}$ alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at positions 9 and 11 may be α, β, or a mixture thereof.

Further, the above derivatives may be compounds having an alkoxy, cycloalkyl, cycloalkyloxy, phenoxy or phenyl group at the end of the ω-chain where the chain is shorter than the primary PGs.

Especially preferred compounds include a 13,14-dihydro-15-keto-PG compound which has a single bond at position 13–14; a 15-keto-16 mono or di-halogen PG compound which has one or two halogen atoms such as chlorine and fluorine at position 16; a 2-decarboxy-2-(2-carboxyethyl)-15-keto-PG compound in which skeletal carbon of a chain is extended by two carbon atoms; and a 15-keto-PGE compound which has an oxo group at position 9 and a hydroxyl group at position 11 of the five membered ring.

A preferred compound used in the present invention is represented by the formula (I):

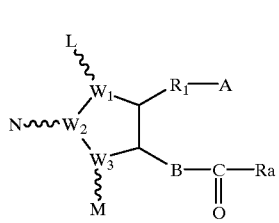

(I)

wherein $W_1$, $W_2$ and $W_3$ are carbon or oxygen atoms;

L, M and N are hydrogen, hydroxy, halogen, lower alkyl, lower alkoxy, hydroxy(lower)alkyl or oxo, wherein at least one of L and M is a group other than hydrogen, and the five-membered ring may have one or more double bond(s);

A is —CH$_2$OH, —COCH$_2$OH, —COOH or its functional derivative;

B is —CH$_2$—CH$_2$—, —CH=CH— or —C≡C—;

$R_1$ is a divalent saturated or unsaturated lower-medium aliphatic hydrocarbon residue, which is unsubstituted or substituted by halogen, alkyl, hydroxy, oxo, aryl or heterocyclic group; and Ra is a saturated or unsaturated lower-medium aliphatic hydrocarbon residue, which is unsubstituted or substituted by halogen, oxo, hydroxy, lower alkyl, lower alkoxy, lower alkanoyloxy, cyclo(lower)alkyl, cyclo(lower)alkyloxy, aryl, aryloxy, heterocyclic group or heterocyclic-oxy group; cyclo(lower)alkyl; cyclo(lower)alkyloxy; aryl; aryloxy; heterocyclic group; or heterocyclic-oxy group.

A group of particularly preferable compounds among the above-described compounds is represented by the general formula (II):

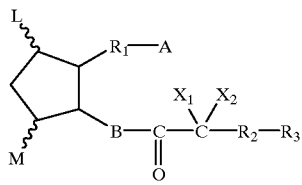

(II)

wherein L, M, $R_1$, A and B are the same definitions described above.

$X_1$ and $X_2$ are hydrogen, lower alkyl or halogen;

$R_1$ is a divalent saturated or unsaturated lower-medium aliphatic hydrocarbon residue, which is unsubstituted or substituted with halogen, oxo, aryl or heterocyclic;

$R_2$ is a single bond or lower alkylene; and $R_3$ is lower alkyl, lower alkoxy, cyclo(lower)alkyl, cyclo(lower)alkyloxy, aryl, aryloxy, heterocyclic or heterocyclic-oxy.

In the above formulae, the term "unsaturated" in the definitions for $R_1$ and $R_a$ is intended to include one or more double bonds and/or triple bonds that are isolatedly, separately or serially present between carbon atoms of the main and/or side chains. An unsaturated bond between two serial positions is represented by denoting the lower number of the two positions, and an unsaturated bond between two distal positions is represented by denoting both of the positions. Preferred unsaturated bonds are a double bond at position 2 and a double or triple bond at position 5.

The term "lower-medium aliphatic hydrocarbon" means a hydrocarbon having a straight or branched chain of 1 to 14 carbon atoms, wherein the side chain has preferably 1 to 3 carbon atoms. The preferred $R_1$ has 1 to 10, more preferably 6 to 10 carbon atoms, and the preferred $R_a$ has 1 to 10, more preferably 1 to 8 carbon atoms.

The term "halogen" includes fluorine, chlorine, bromine and iodine.

The term "lower" means a group having 1 to 6 carbon atoms unless otherwise specified.

The term "lower alkyl" means a straight- or branched-chain saturated hydrocarbon group having 1 to 6 carbon atoms, for example, methyl, ethyl, propyl, isopropyl, butyl, isobutyl, t-butyl, pentyl and hexyl.

The term "lower alkoxy" means a lower alkyl-O-wherein the lower alkyl is as defined above.

The term "hydroxy(lower)alkyl" means a lower alkyl as defined above, which is substituted by at least one hydroxyl group, for example, hydroxymethyl, 1-hydroxyethyl, 2-hydroxyethyl and 1-methyl-1-hydroxyethyl.

The term "lower alkanoyloxy" means a group represented by the formula RCO—O—, wherein RCO— is an acyl formed by oxidation of a lower alkyl as defined above, for example, acetyl.

The term "cyclo(lower)alkyl" means a group formed by cyclization of a lower alkyl group as defined above but contains 3 or more carbon atoms, for example, cyclopropyl, cyclobutyl, cyclopentyl and cyclohexyl.

The term "cyclo(lower)alkyloxy" means a group represented by the formula cyclo(lower)alkyl—O—, wherein cyclo(lower)alkyl is as defined above.

The term "aryl" includes optionally substituted aromatic hydrocarbon ring, preferably monocyclic group, for example, phenyl, naphthyl, tolyl and xylyl. Examples of the substituents include halogen, lower alkoxy and halo(lower)alkyl group, wherein halogen atom and lower alkyl group are as defined above.

The term "aryloxy" means a group represented by the formula ArO—, wherein Ar is an aryl group as defined above.

The term "heterocyclic group" includes mono- to tricyclic, preferably monocyclic heterocyclic group which is 5 to 14, preferably 5 to 10 membered ring having optionally substituted carbon atom and 1 to 4, preferably 1 to 3 of 1 or 2 kinds of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazyl, pyrimidinyl, pyrazyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, puryl, quinazolinyl, carbazolyl, acridinyl, phenanthridinyl, benzimidazolyl, benzimidazolonyl, benzothiazolyl and phenothiazinyl. Examples of the substituent in this case include halogen and halogen substituted lower alkyl, wherein halogen atom and lower alkyl are as defined above.

The term "heterocyclic-oxy group" means a group represented by the formula HcO—, wherein Hc is a heterocyclic group as defined above.

The term "functional derivative" of A includes salts (preferably pharmaceutically acceptable salts), ethers, esters and amides.

Examples of suitable "pharmaceutically acceptable salts" include commonly used nontoxic salts such as salts with inorganic bases, for example, alkali metal salts (sodium salt, potassium salt and the like); alkaline earth metal salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt and caffeine salt); basic amino acid salts (such as arginine salt and lysine salt); tetraalkyl ammonium salts and the like. These salts may be manufactured from, for example, corresponding acids and bases in accordance with a conventional manner or by the salt exchange process.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; medium or higher alkyl ethers such as octyl ether, diethylhexyl ether, lauryl ether and cetyl ether; unsaturated ethers such as oleyl ether and linolenyl ether; lower alkenyl ethers such as vinyl ether and allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl esters such as hydroxyethyl ester; and lower alkoxy(lower)alkyl esters such as methoxymethyl ester and 1-methoxyethyl ester, and as well as, for example, optionally substituted aryl esters such as phenyl ester, tolyl ester, t-butylphenyl ester, salicyl ester, 3,4-dimethoxyphenyl ester and benzamidephenyl ester; and aryl(lower)alkyl esters such as benzyl ester, trityl ester and benzhydryl ester. Examples of amides include mono- or di-lower alkyl amides such as methylamide, ethylamide and dimethylamide; aryl amides such as anilide and toluidide; and alkyl or aryl sulfonyl amides such as methylsulfonyl amide, ethylsulfonyl amide and tolylsulfonyl amide.

Preferred examples of L and M include hydroxy and oxo and especially, M is hydroxy and L is oxo which provides the 5-membered ring structure of, so called, PGE type.

Preferred examples of A-group include —COOH and its pharmaceutically acceptable salts, esters and amides.

Preferred example of B is —CH$_2$—CH$_2$—which provides the structure of so-called, 13,14-dihydro type.

Preferred example of X$_1$ and X$_2$ is that at least one of them is halogen, more preferably, both of them are halogen, especially, fluorine that provides a structure of, so called 16,16-difluoro type.

Preferred R$_1$ is a hydrocarbon containing 1–10 carbon atoms, preferably 6–10 and more preferably 8 carbon atoms.

Examples of R$_1$ include, for example, the following residues:

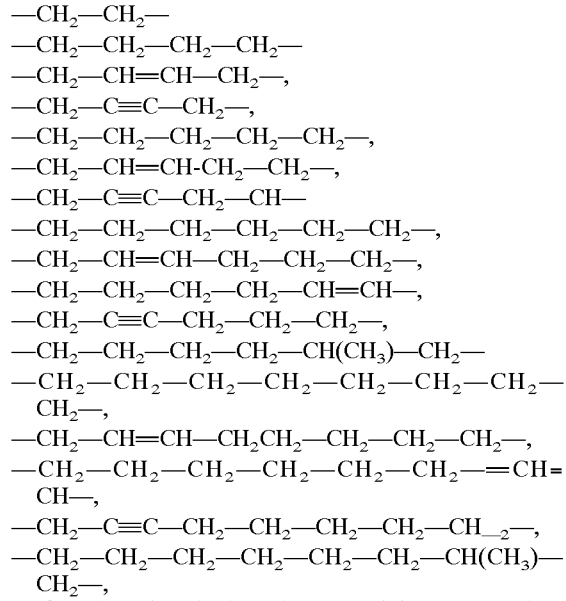

—CH$_2$—CH$_2$—
—CH$_2$—CH$_2$—CH$_2$—CH$_2$—
—CH$_2$—CH=CH—CH$_2$—,
—CH$_2$—C≡C—CH$_2$—,
—CH$_2$—CH$_2$—CH$_2$—CH$_2$—CH$_2$—,
—CH$_2$—CH=CH-CH$_2$—CH$_2$—,
—CH$_2$—C≡C—CH$_2$—CH—
—CH$_2$—CH$_2$—CH$_2$—CH$_2$—CH$_2$—CH$_2$—,
—CH$_2$—CH=CH—CH$_2$—CH$_2$—CH$_2$—,
—CH$_2$—CH$_2$—CH$_2$—CH$_2$—CH=CH—,
—CH$_2$—C≡C—CH$_2$—CH$_2$—CH$_2$—,
—CH$_2$—CH$_2$—CH$_2$—CH$_2$—CH(CH$_3$)—CH$_2$—
—CH$_2$—CH$_2$—CH$_2$—CH$_2$—CH$_2$—CH$_2$—CH$_2$—CH$_2$—,
—CH$_2$—CH=CH—CH$_2$CH$_2$—CH$_2$—CH$_2$—CH$_2$—,
—CH$_2$—CH$_2$—CH$_2$—CH$_2$—CH$_2$—CH$_2$—=CH=CH—,
—CH$_2$—C≡C—CH$_2$—CH$_2$—CH$_2$—CH$_2$—CH$_2$—,
—CH$_2$—CH$_2$—CH$_2$—CH$_2$—CH$_2$—CH$_2$—CH(CH$_3$)—CH$_2$—,

Preferred Ra is a hydrocarbon containing 1–10 carbon atoms, more preferably, 1–8 carbon atoms. Ra may have one or two side chains having one carbon atom.

The configuration of the ring and the α- and/or ω chains in the present invention may be the same as or different from that of the primary PGs. However, the present invention also includes a mixture of a compound having a primary type configuration and a compound of a non-primary type configuration.

When a 15-keto-PG compound of the present invention has, for example, a single bond between carbon atom number 13 and 14, the compound may be in the keto-hemiacetal equilibrium by formation of a hemiacetal between hydroxy at position 11 and oxo at position 15.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the compounds used in the invention include both isomers. Further, while the compounds used in the invention may be represented by a structure formula or name based on keto-type regardless of the presence or absence of the isomers, it is to be noted that such structure or name does not intend to exclude the hemiacetal type compound.

In the present invention, any of the individual tautomeric isomers and mixtures thereof, or optical isomers and mixtures thereof, racemic mixtures and other isomers such as steric isomers may be used in the same purpose.

Some of the compounds used in the present invention may be prepared by the method disclosed in U.S. Pat. Nos. 5,073,569, 5,166,174, 5,221,763, 5,212,324 and 5,739,161 and U.S. patent application Ser. No. 09011218 (these cited references are herein incorporated by reference).

The compounds used in the present invention may be used as drugs for animals and human beings and can be applied systemically or topically. Usually, it is administered by oral administration, intravenous injection (including infusion), subcutaneous injection, intra rectal administration, intra vaginal administration and the like. The dose may vary depending on the strain of the patient, i.e. particular animal or human, age, body weight, symptom to be treated, desired therapeutic effect, administration route, term of treatment and the like. A satisfactory effect can be obtained by systemic administration 2–4 times per day or continuous administration at the amount of 0.001–500 mg/kg per day.

The bile secretion promoting composition of the present invention can be formulated as a composition for oral administration, for injection, for perfusion or for external administration, tablet, sublingual, suppository, and vaginal suppository.

The composition of the present invention may be admixed with pharmaceutically acceptable additives. In the present specification, the term "additive" refers an ingredient being contained in the composition together with the 15-keto-prostaglandin compound, and may include for example, excipient, diluent, filler, solvent, lubricant, adjuvant, binder, disintegrator, coating agent, capuslating agent, ointment base, suppository base, aerozoling agent, emulsifier, dispersant, suspending agent, viscosity-increasing agent, tonicity agent, buffering agent, soothing agent, preservative, anti oxidant, corrigent, odor corrigent, flavor, colorant, and a functional material (for example, cyclodextrin or biodegradable polymer.) Details of the additives have been described in general reference books of pharmaceutics, and may be selected from those described.

The amount of the 15-keto-prostaglandin compound contained in the bile secretion promoting composition of the invention may vary depending on the formulation of the composition, and may generally be 0.0001–10.0 wt %, more preferably, 0.001–1.0 wt %.

Examples of solid compositions for oral administration include tablets, troches, sublingual tablets, capsules, pills, powders, granules and the like. The solid composition may be prepared by mixing one or more active ingredients with at least one inactive diluent, e.g. lactose, mannitol, glucose, hydroxypropyl cellulose, fine crystalline cellulose, starch, polyvinyl pyrrolidone and magnesium aluminometasilicate. The composition may further contain additives other than the inactive diluent, for example, lubricants e.g., magnesium stearate, a disintegrator e.g. cellulose calcium gluconates, stabilizers e.g. α-, β- or γ-cyclodextrin, ether cyclodextrins, e.g. dimethyl-γ-, dimethyl-β-, trimethyl-β- or hydroxypropyl-β-cyclodextrins, branched cyclodextrins, e.g. glucosyl- or maltosyl-cyclodextrins, formyl cyclodextrin, sulfur-containing cyclodextrin, misoprotol or phospholipids. When a cyclodextrin is used as a stabilizer, the active ingredient may form an inclusion compound with the cyclodextrin to improve the stability. The stability may also be improved by including the ingredient in liposome made from phospholipid. Tablets and pills may be coated with an enteric or gastroenteric film e.g. white sugar, gelatin, hydroxypropylcellulose, hydroxypropylmethyl cellulose phthalates and the like, if necessary. They may be covered with two or more layers. Additionally, the composition may be capsulated by means of an easily degradable material such as gelatin. Sublingual tablet is preferable, when an immediate effect is desired.

Base of the composition may be glycerin, lactose and the like. Examples of liquid compositions for oral administration include emulsions, solutions, suspensions, syrups, elixirs and the like. Said compositions may further contain a conventionally used inactive diluent e.g. purified water or ethyl alcohol. The composition may contain additives other than the inactive diluent such as adjuvant e.g. wetting agents and suspending agents, sweeteners, flavors, fragrance and preservatives.

The composition of the present invention may be in the form of spraying composition which contains one or more active ingredients and may be prepared according to a known method.

Examples of the injectable compositions of the present invention for parenteral administration include sterile aqueous or nonaqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

Another formulation of the composition according to the present invention may be rectal or vaginal suppository. Said suppository may be prepared by mixing at least one active compound according to the invention with a suppository base e.g. cacao butter and may optionally be admixed with a nonionic surfactant having a suitable softening temperature to improve absorption.

The term "treatment" used herein refers to any means of control of a condition including prevention, care, relief of the condition, and arrestation or relief of development of the condition. When used in the context of "treatment of a liver" and the like, the term "treatment" or "treating" refers to any means of contacting a liquid composition with the liver, including perfusing or rinsing the liver with the liquid composition and preserving the liver in the liquid composition.

When the compound used in this invention is employed in a liver transplantation process, it may be administered to the body as described above or may be used for treatment of the liver to be transplanted.

When applied for treatment of the liver to be transplanted, the composition of the invention may be used as a perfusate to perfuse said liver during the extirpation process, as a preservation solution for the removed liver, and a rinse solution for rinsing the liver before blood reperfusion. The compound used in the present invention may be added to anyone of the perfusate, the preservation solution and the rinse solution, or to two or three of them.

The present composition for liver transplantation may be formulated as a liquid composition, or a solid composition to be dissolved before use. Said solid composition may be dissolved, suspended or emulsified in a purified water or saline before use. Solid composition may be tablet, granule, powder and the like and may be prepared according to a known procedure. Said solid composition may contain conventional additives such as excipient, binder, disintegrant, dispersing agent, reabsorbent, buffering agent, surfactant, solubilizer, preservative, emulsifier, tonicity agent, stabilizer and pH controller. In addition, any other preserving agent used for liver treatment in a conventional liver transplantation procedure may be added to the composition insofar as it does not contrary to the object of the present invention.

In addition, the composition for treatment of liver to be transplanted may be dissolved in a conventional solution for organ transplantation such as Euro Collins solution (EC solution), Wisconsin solution (U-W solution) and Krebs-Ringer solution before use.

The concentration of the 15-keto-PG compound in the composition for liver treatment may vary depending on kind of the compound, state of the liver, time period for the treatment and the like and in general, the final concentration may be about 0.001 μM/L–1000 μM/L, preferably about 0.1 μM/L–100 μM/L.

The bile secretion promoting composition of the present invention may be employed in treatment of various conditions and diseases caused by deficiency of bile secretion. The composition has an ability to promote bile secretion irrespective of the presence or absence of bile acid. Further, the composition may be employed in liver transplantation as a liver preservation solution, a perfusate, or a rinse solution.

The bile secretion promoting composition of the present invention may further be admixed with any other active ingredients insofar as it does not contrary to the object of the present invention.

EXAMPLE

The present invention will be illustrated in more detail by way of the following examples. These examples should not be used as any limitation of the present invention.

Test Example 1

Test Method

Male Wister rats were used. 100 μg/kg of test compound 1 (13,14-dihydro-15-keto-16, 16-difluoro-18(S)-methyl-prostaglandin $E_1$) was administered orally to the test group animals (n=8) 3 times a day for 7days. To the control group animals (n=7), the same volume of the vehicle, i.e. 0.01% polysorbate 80, 0.5% ethanol in distilled water was administered. At the next day after the final administration (day 8), the common bile duct of the respective rat was cannulated under ether anesthesia and the rat was placed in ball man gauge for 1 hour to recover from anesthesia. The bile discharged over one hour time period, i.e. from 1 to 2 hours of the cannulation, was collected and determined bile flow.

Result

Effect of the test compound 1 on normal rat bile flow is shown in FIG. 1.

As is understood from the result, the normal rat bile flow was significantly increased by test compound 1 administration.

Test Example 2

Test Method

Male Wister rats were used. Each rat was cannulated for collection of bile under pentobarbital sodium anesthesia. A catheter was inserted and fixed in the portal vein. Krebs-Ringer solution saturated with 95% $O_2$ and 5% $CO_2$ (pH 7.4, 37° C.) was infused via the catheter at a constant flow rate of 4.0 ml/min/g liver weight by means of peristaltic pump to perfuse the liver. The liver was removed under perfusion. In case where the bile secretion was necessary to maintain being the physiological level, the liver was perfused with Krebs-Ringer solution supplemented with sodium taurocolate (30 μmol/l). For the test group animals, the test compound 1 was added to the Krebs-Ringer solution. Bile of the each animals including test and control groups was collected in every 5 minutes.

Result

Figure 2:
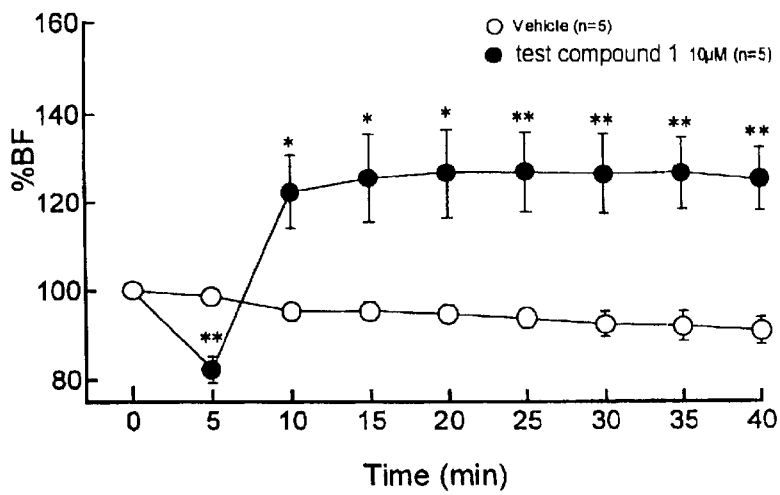
FIGS. 2 A–C represent the result of the Test Example 2; 2A shows time course of bile flow (BF) when 10 μM of the test compound 1 was added under the presence of bile acid; 2B shows dose dependent cholagogic effect of the test compound 1 under the presence of bile acid; and 2C shows the bile secretion in response to the test compound 1, difference between those under presence (TC(+)) and absence (TC(−)) of bile acid is shown.
Figure 2:
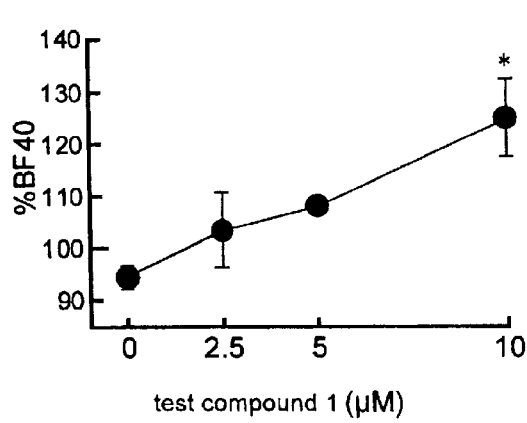
Figure 2:
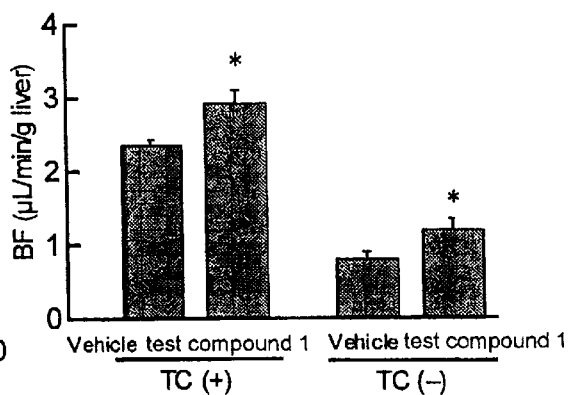

Effect of the test compound 1 on bile flow of perfused rat liver is shown in FIG. 2A, FIG. 2B and FIG. 2C. Fig 2A shows time course of bile flow (BF) when 10 μM of the test compound 1 was added under the presence of bile acid. FIG. 2B shows dose dependent cholagogic effect of the test compound 1 under the presence of bile acid. FIG. 2 C shows the bile secretion in response to the test compound 1, difference between under the presence (TC(+)) or absence (TC(−)) of bile acid.

According to the results shown below, the test compound 1 significantly increased bile flow of the perfused rat liver. The test compound 1 increased the bile flow irrespective of the presence or absence of bile acid.

Test Example 3

Test Method

Isolated perfused liver sample was prepared by the same manner as described in the test example 2. Each livers of test and control groups was perfused with Krebs-Ringer solution saturated with 95% $N_2$ and 5% $CO_2$ for 20 minutes to expose the liver oxygen-free condition. After that, Krebs-Ringer solution saturated with 95% $O_2$ and 5% $CO_2$ was perfused to re-oxygenize the liver. At the re-oxygenization step, 10 μM of the test compound 1 was added to the Krebs-Ringer solution for the test group.

Result

Figure 3:
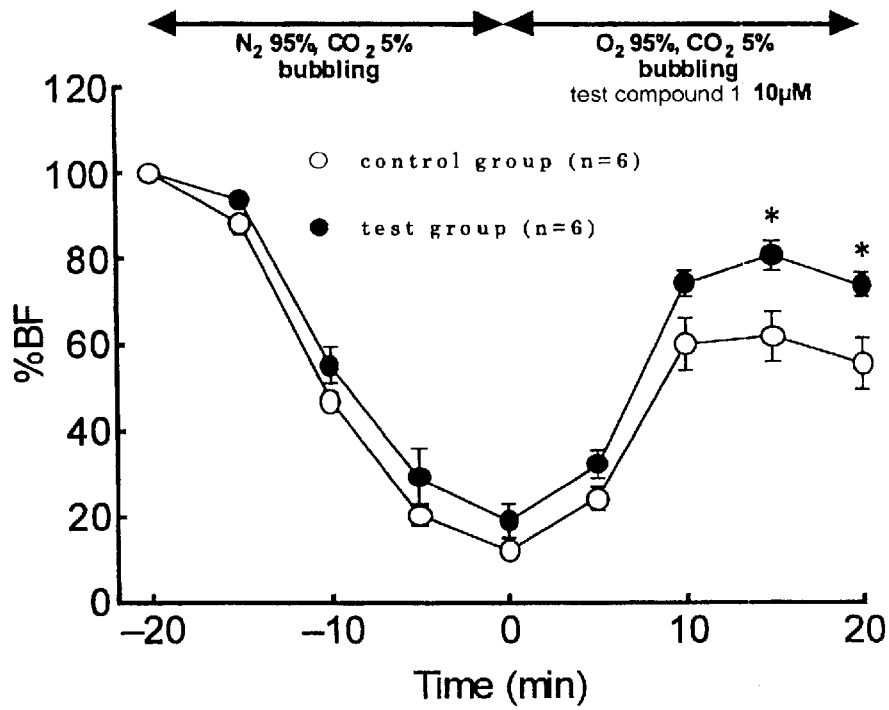
FIG. 3 represents the result of the Test Example 3; effect of the test compound 1 on bile flow recovery of anoxia/re-oxygenation perfused rat liver.

Effect of the test compound 1 on bile flow recovery of anoxia/re-oxygenation perfused rat liver is shown in FIG. 3.

As is revealed from the result, the bile flow (BF) was reduced to 20% by the anoxia treatment compared with the BF before the treatment (100%). Then, re-oxygenation with a solution admixed with the test compound I was significantly increased the bile flow than those with the vehicle.

Test Example 4

Test Method

Male Wister Rats were anesthetized with pentobarital sodium and hepatic-portal region was exposed by abdominal midline incision. The common bile duct was cannulated and the portal stem was inserted with a 19 gauge surflo® needle equipped with a three way stopcock. Immediately, the liver was perfused with oxidized Krebs-Ringer Buffer at a rate of 4.0 ml/min/g liver and was bleeded from the inferior vena cava. Treitz' ligament, the ligament around the liver, and diaphragm were cut and the liver was removed to the outside of the body and subjected to extracoporeal perfusion. The liver was subjected to a fifteen minutes of pre-perfusion until its oxygen consumption achieved to constant and then, the perfusate was exchanged with University of Wisconsin solution (U-W solution) at 4° C. Immediately after finish of the exchange, the liver connected with the three-way stopcock was removed from the perfusion cycle and the inlet was clamped. Then the liver was putted into the U-W solution at the same temperature and stored for 16 hours. (It has been reported that after this time period of storage, oxygen radicals are generated within 15 minutes from the onset of reperfusion and the amount of basic bile secretion reduces significantly; Hepatology Vol. 30, No. 6, 1454–1463, 1999, The cited reference is herein incorporated by reference.) After the 16-hour storage, the liver was reperfused with Krebs-Ringer solution for 40 minutes. During the reperfusion period, bile flow was determined every 5 minutes.

In the above perfusion protocol, 10 μM of test compound 1 or test compound 2 (13,14-dihydro-15-keto-16,16-difluoro-17(R)-methyl-prostaglandin $E_1$) were added to the U-W solution to determine the effects of these drugs on recovery of bile flow.

Result

Figure 4:
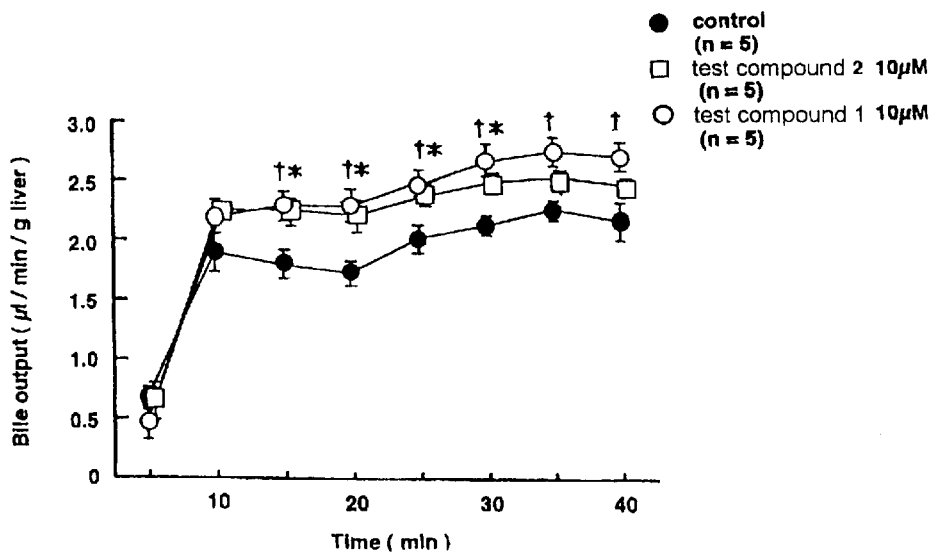
FIG. 4 represents result of the Test Example 4, effect of the test compound 1 and 2 (13,14-dihydro-15-keto-16,16-difluoro-17 (R)-methyl-prostaglandin $E_1$) on the bile flow of a rat isolated liver when added to the preservation solution for the liver.

Effect of the test compound 1 and the test compound 2 on the bile flow of a rat isolated live when added to the preservation solution for the liver is shown in the FIG. 4.

According to the following result, addition of test compound 1 and test compound 2 to the liver preservation solution increased the bile flow at the reperfusion step significantly.

Test Example 5

Test Method

The perfusion protocol of the Test Example 4 was repeated except for the test compound 1 and the test compound 2 were added to the Krebs-Ringer solution, i.e. the rinse solution perfused for 40 minute's to determine the recovery of the bile flow.

Result

Figure 5:
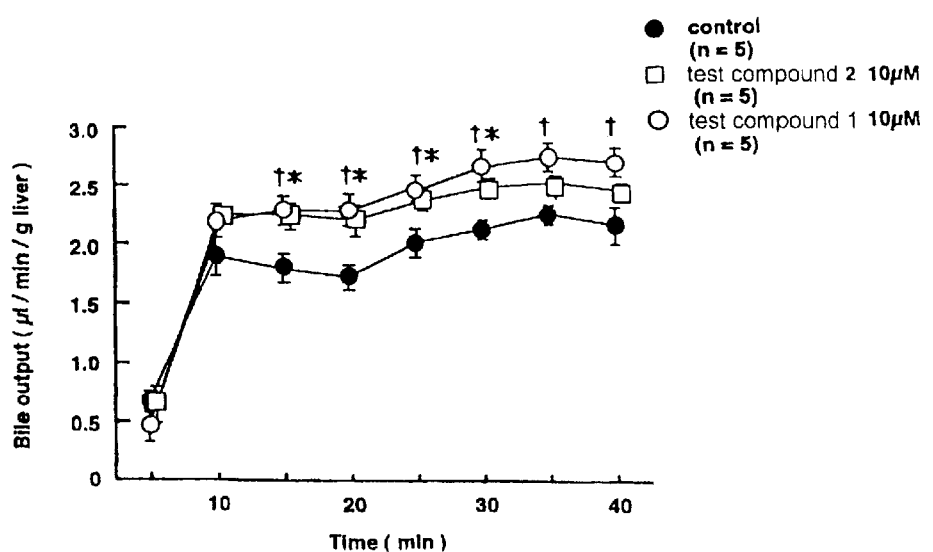
FIG. 5 represents result of the Test Example 5; effect of the test compounds 1 and 2 on bile flow in a rat isolated liver when added to the rinse solution.

Effects of the test compound 1 and the test compound 2 on bile flow of a rat isolated liver when added to the rinse solution is shown in FIG. 5.

The result indicated that the bile flow in reperfusion of cold preserved rat liver is significantly increased by addition of the test compound 1 and the test compound 2 to the rinse solution.

Industrial Applicability

The compound used in the present invention is useful as a bile secretion promoter and therefore, it will be useful for treatment or prophylaxis of various diseases and conditions caused by or associated with bile secretion deficient, and also be useful in liver transplantation process as a liver preservation solution, a perfusate and a rinse solution or an agent for treatment after implantation of the liver.

What is claimed is:

1. A method for promoting bile secretion comprising administering an effective amount of a 15-keto-prostaglandin compound represented by the general formula (I):

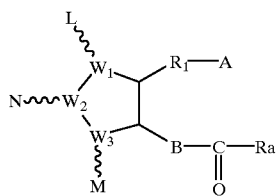

(I)

wherein $W_1$, $W_2$ and $W_3$ are carbon or oxygen atoms;

L, M and N are hydrogen, hydroxy, halogen, lower alkyl, lower alkoxy, hydroxy(lower)alkyl or oxo, wherein at least one of L and M is a group other than hydrogen, and the five-membered ring may have one or more double bond(s);

A is —$CH_2OH$, —$COCH_2OH$, —COOH or its functional derivative;

B is —$CH_2$—$CH_2$—, —CH=CH= or —C≡C—;

$R_1$ is a divalent saturated or unsaturated lower-medium aliphatic hydrocarbon residue, which is unsubstituted or substituted by halogen, alkyl, hydroxy, oxo, aryl or heterocyclic group; and Ra is a saturated or unsaturated lower-medium aliphatic hydrocarbon residue, which is unsubstituted or substituted by halogen, oxo, hydroxy, lower alkyl, lower alkoxy, lower alkanoyloxy, cyclo(lower)alkyl, cyclo(lower)alkyloxy, aryl, aryloxy, heterocyclic group or heterocyclic-oxy group; cyclo(lower)alkyl; cyclo(lower)alkyloxy; aryl; aryloxy; heterocyclic group; or heterocyclic-oxy group, to a subject having a condition or disease associated with bile secretion deficiency.

2. The method of claim 1, wherein the 15-keto-prostaglandin compound is a 13,14-dihydro-15-keto-prostaglandin compound.

3. The method of claim 1, wherein the 15-keto-prostaglandin compound is a 15-keto-16-mono or di-halogen-prostaglandin compound.

4. The method of claim 1, wherein the 15-keto-prostaglandin compound is a 13,14-dihydro-15-keto-16-mono or di-halogen-prostaglandin compound.

5. The method of claim 1, wherein the 15-keto-prostaglandin compound is a 15-keto-16-mono or di-fluoro-prostaglandin compound.

6. The method of claim 1, wherein the 15-keto-prostaglandin compound is a 13,14-dihydro-15-keto-16-mono or di-fluoro-prostaglandin compound.

7. The method of claim 1, wherein the 15-keto-prostaglandin compound is a 15-keto-prostaglandin E compound.

8. The method of claim 1, wherein the 15-keto-prostaglandin compound is 13,14-dihydro-15-keto-16,16-difluoro-18-methyl-prostaglandin $E_1$.

9. The method of claim 1, wherein the 15-keto-prostaglandin compound is 13,14-dihydro-15-keto-16,16-difluoro-17-methyl-prostaglandin $E_1$.

10. A method for treating a liver to be transplanted in a liver transplantation process, which comprises contacting the liver with a liquid composition comprising a 15-keto-prostaglandin compound represented by the general formula (I):

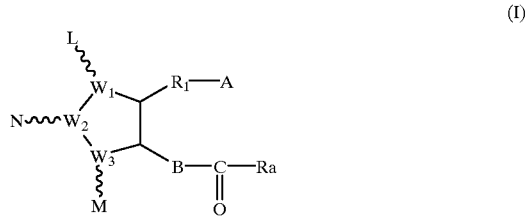

(I)

wherein $W_1$, $W_2$ and $W_3$ are carbon or oxygen atoms;

L, M and N are hydrogen, hydroxy, halogen, lower alkyl, lower alkoxy, hydroxy(lower)alkyl or oxo, wherein at least one of L and M is a group other than hydrogen, and the five-membered ring may have one or more double bond(s);

A is —$CH_2OH$, —$COCH_2OH$, —COOH or its functional derivative;

B is —CH₂—CH₂—, —CH=CH— or —C≡C—;

R₁ is a divalent saturated or unsaturated lower-medium aliphatic hydrocarbon residue, which is unsubstituted or substituted by halogen, alkyl, hydroxy, oxo, aryl or heterocyclic group; and Ra is a saturated or unsaturated lower-medium aliphatic hydrocarbon residue, which is unsubstituted or substituted by halogen, oxo, hydroxy, lower alkyl, lower alkoxy, lower alkanoyloxy, cyclo(lower)alkyl, cyclo(lower)alkyloxy, aryl, aryloxy, heterocyclic group or heterocyclic-oxy group; cyclo(lower)alkyl; cyclo(lower)alkyloxy; aryl; aryloxy; heterocyclic group; or heterocyclic-oxy group.

11. The method of claim 10, wherein the 15-keto-prostaglandin compound is a 13,14-dihydro-15-keto-prostaglandin compound.

12. The method of claim 10, wherein the 15-keto-prostaglandin compound is a 15-keto-16-mono or dihalogen-prostaglandin compound.

13. The method of claim 10, wherein the 15-keto-prostaglandin compound is a 13,14-dihydro-15-keto-16-mono or di-halogen-prostaglandin compound.

14. The method of claim 10, wherein the 15-keto-prostaglandin compound is a 15-keto-16-mono or di-fluoro-prostaglandin compound.

15. The method of claim 10, wherein the 15-keto-prostaglandin compound is a 13,14-dihydro-15-keto-16-mono or di-fluoro-prostaglandin compound.

16. The method of claim 10, wherein the 15-keto-prostaglandin compound is a 15-keto-prostaglandin E compound.

17. The method of claim 10, wherein the 15-keto-prostaglandin compound is 13,14-dihydro-15-keto-16,16-difluoro-18-methyl-prostaglandin $E_1$.

18. The method of claim 10, wherein the 15-keto-prostaglandin compound is 13,14-dihydro-15-keto-16,16-difluoro-17-methyl-prostaglandin $E_1$.

19. The method of claim 10, wherein the liquid composition is a preservation solution.

20. The method of claim 10, wherein the liquid composition is a perfusate.

21. The method of claim 10, wherein the liquid composition is a rinse solution.

* * * * *